United States Patent
Yamamoto et al.

(10) Patent No.: US 12,031,947 B2
(45) Date of Patent: Jul. 9, 2024

(54) SONIC INSPECTION DEVICE, SONIC INSPECTION METHOD, AND CONTACT MEMBER

(71) Applicants: KABUSHIKI KAISHA TOSHIBA, Tokyo (JP); TOSHIBA ENERGY SYSTEMS & SOLUTIONS CORPORATION, Kawasaki (JP)

(72) Inventors: Noriko Yamamoto, Yokohama Kanagawa (JP); Akiko Hirao, Kawasaki Kanagawa (JP); Tomio Ono, Yokohama Kanagawa (JP); Yutaka Nakai, Yokohama Kanagawa (JP); Tsuyoshi Kobayashi, Kawasaki Kanagawa (JP)

(73) Assignees: KABUSHIKI KAISHA TOSHIBA, Tokyo (JP); TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 25 days.

(21) Appl. No.: 17/686,831

(22) Filed: Mar. 4, 2022

(65) Prior Publication Data

US 2023/0079884 A1    Mar. 16, 2023

(30) Foreign Application Priority Data

Sep. 16, 2021   (JP) ................. 2021-151511
Feb. 14, 2022   (JP) ................. 2022-020134

(51) Int. Cl.
*G01N 29/04*  (2006.01)
*A61B 8/00*  (2006.01)

(52) U.S. Cl.
CPC ......... *G01N 29/041* (2013.01); *A61B 8/4281* (2013.01); *A61B 8/4444* (2013.01); *G01N 2291/044* (2013.01)

(58) Field of Classification Search
CPC .......... G01N 29/041; G01N 2291/044; G01N 29/043; G01N 29/265; G01N 29/11;
(Continued)

(56) References Cited

U.S. PATENT DOCUMENTS 3,921,442 A * 11/1975 Soloway ................ G01N 29/28
                                                          73/644
4,143,553 A *  3/1979 Martens ............. G01N 29/2487
                                                          73/636
(Continued)

FOREIGN PATENT DOCUMENTS

JP    2020-053956 A    4/2020
JP    2021-067603 A    4/2021
WO    WO-2017/024704 A1    2/2017

*Primary Examiner* — Tarun Sinha
(74) *Attorney, Agent, or Firm* — Foley & Lardner LLP (57) ABSTRACT

A sonic inspection device according to an embodiment includes: a sonic probe that includes a transducer configured to perform at least one of transmitting a sound wave and receiving a sound wave and has a sonic function surface constituting at least one of a transmitting surface of the sound wave and a receiving surface of the sound wave; a contact member that includes a couplant and a sheet-shaped member, the couplant having a first surface, which is in contact with the sonic function surface of the sonic probe directly or while interposing an intermediate member, and a second surface on an opposite side of the first surface, and containing an elastomer, and the sheet-shaped member laminated with the couplant to be in contact with the second surface and containing a polymer; and a loading mechanism configured to apply a load to the contact member.

13 Claims, 4 Drawing Sheets

(58) Field of Classification Search
CPC .... G01N 29/28; A61B 8/4281; A61B 8/4444; A61B 8/4483
See application file for complete search history.

(56) References Cited

U.S. PATENT DOCUMENTS

| | | | | |
|---|---|---|---|---|
| 4,186,747 | A * | 2/1980 | Linuma | A61B 8/0825 128/915 |
| 5,097,710 | A * | 3/1992 | Palynchuk | G01N 29/28 73/644 |
| 7,360,427 | B2 * | 4/2008 | Drinkwater | G01N 29/28 73/635 |
| 7,694,570 | B1 * | 4/2010 | Dam | H10N 30/00 73/644 |
| 2010/0154560 | A1 * | 6/2010 | Mueller | G10K 11/02 29/25.35 |
| 2017/0272865 | A1 | 9/2017 | Zho et al. | |
| 2021/0123890 | A1 | 4/2021 | Hirao et al. | |

* cited by examiner

SONIC INSPECTION DEVICE, SONIC INSPECTION METHOD, AND CONTACT MEMBER

CROSS REFERENCE TO RELATED APPLICATION

This application is based upon and claims the benefit of priority from Japanese Patent Application No. 2021-151511, filed on Sep. 16, 2021 and No. 2022-020134, filed on Feb. 14, 2022; the entire contents of which are incorporated herein by reference.

FIELD

Embodiments disclosed herein relate to a sonic inspection device, a sonic inspection method, and a contact member.

BACKGROUND

A sonic inspection device using propagation of sound waves such as ultrasonic waves and elastic waves is used for inspecting various members, devices, infrastructures, and so on. An ultrasonic inspection device is also used for medical diagnosis and the like. In the case where a sonic inspection probe used in such inspection devices, such as a sonic receiver, a sonic transmitter, or a sonic transmitter-receiver represented by an ultrasonic probe, an AE (acoustic emission) sensor, or the like is installed on an object to be inspected, a liquid or viscous couplant such as glycerin or vaseline is interposed between the object to be inspected and a sonic function surface of the probe, that constitutes at least one of a transmitting surface or a receiving surface of sound waves so that the sound waves are efficiently propagated between the probe and the object to be inspected.

The aforesaid couplant is important for efficiently transmitting sound waves such as ultrasonic waves from the probe to the object to be inspected or from the object to be inspected to the probe and increasing test accuracy. However, processes of applying and removing the liquid or viscous couplant are troublesome. This is a factor to increase the inspection time and man-hour. Further, some objects to be inspected of an inspection object may be contaminated by the couplant, in which case the inspection itself cannot be conducted.

A solid couplant has also been proposed, but it is far poorer in ultrasonic propagation than the liquid couplant. A possible reason for this is that, between the couplant of the probe and the object to be inspected, the air whose acoustic impedance is greatly different is present. An adhesive solid couplant has also been proposed to avoid the presence of air between an installation surface of the couplant for sonic inspection and the object to be inspected. However, the installation surface of the couplant for sonic inspection is in close contact with the object to be inspected, and the couplant for sonic inspection cannot be slid when the conventional adhesive solid couplant is used. Therefore, even when an installation position is moved by a small distance, it is necessary to once peel off the probe along with the couplant from the object to be inspected, which makes the inspection process complicated.

DETAILED DESCRIPTION

A sonic inspection device of an embodiment includes: a sonic probe including a transducer configured to perform at least one of transmitting a sound wave and receiving a sound wave, and that has a sonic function surface constituting at least one of a transmitting surface of the sound wave and a receiving surface of the sound wave; a contact member including a couplant and a sheet-shaped member, the couplant having a first surface, which is in contact with the sonic function surface of the sonic probe directly or while interposing an intermediate member, and a second surface on an opposite side of the first surface, and containing an elastomer, and the sheet-shaped member laminated with the couplant to be in contact with the second surface and containing a polymer; and a loading mechanism configured to apply a load to the contact member.

A sonic inspection device, a sonic inspection method, and a contact member for the sonic inspection device of embodiments will be described below with reference to the drawings. Note that, in each embodiment, substantially the same constituent parts are denoted by the same reference signs and a description thereof may be partly omitted. The drawings are schematic, and a relation of a thickness and planar dimension of each part, a thickness ratio among the parts, and so on may be different from actual ones. In the description, a term expressing an up-down direction indicates a relative direction when an inspection surface of an object to be inspected is defined as an upper side and may be different from an actual direction based on a gravitational acceleration direction.

Figure 1:
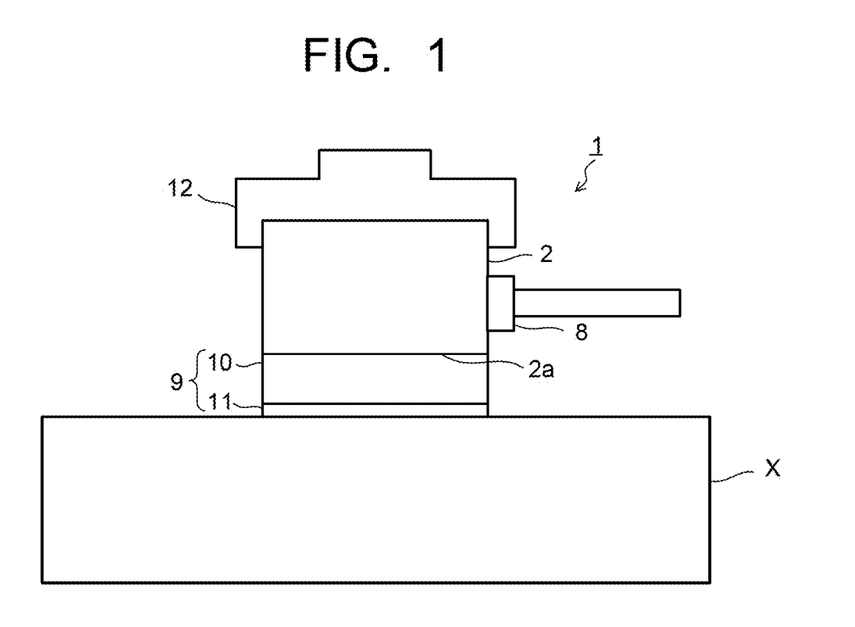
FIG. 1 is a diagram illustrating a constitution of a sonic inspection device of an embodiment.

FIG. 1 is a diagram illustrating the sonic inspection device of the embodiment. A sonic inspection device 1 illustrated in FIG. 1 has a vertical sonic probe 2. The sonic inspection device 1 has, for example, the pulse-reflection type sonic probe 2, conducts a nondestructive inspection, such as flaw detection, by measuring sound waves (reflected waves) returning from an inspection object such as a flaw in the object to be inspected. The sonic probe 2 may conduct the nondestructive inspection, such as the flaw detection, by measuring the sound waves generated by the inspection object. The sonic probe 2 has at least one of the functions of transmission and reception of sound waves, and its concrete examples include an ultrasonic transmitter-receiver (ultrasonic transducer) and a sonic receiver. Typical examples of the ultrasonic transmitter-receiver include an ultrasonic probe. Typical examples of the sonic receiver include an AE sensor. The sonic probe 2 may be a sonic transmitter.

The sound wave mentioned here is a generic name of any elastic vibration waves propagating through an elastic body regardless of whether it is gas, liquid, or solid and includes not only sound waves in an audible frequency range but also ultrasonic waves having a frequency higher than the audible frequency range, low-frequency sounds having a frequency lower than the audible frequency range, and so on. The frequency of the sound waves is not particularly limited and includes high frequencies to low frequencies. In the sonic inspection device 1 of the embodiment, the sonic probe 2 has a transmitting and receiving surface, a receiving surface, a transmitting surface, and the like of sound waves. Here, the surface of the sonic probe 2 constituting at least one of the transmitting surface and the receiving surface of sound waves will be called a sonic function surface. The sonic probe 2 includes such a sonic function surface 2a.

Figure 2:
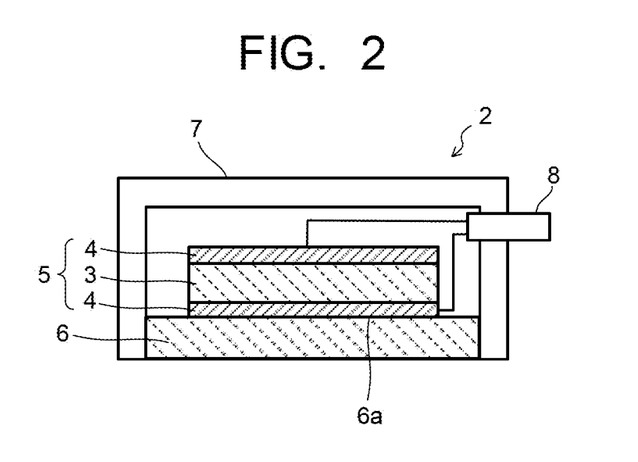
FIG. 2 is a cross-sectional diagram illustrating a sonic probe in the sonic inspection device illustrated in FIG. 1.

In the sonic inspection device 1 illustrated in FIG. 1, the sonic probe 2 is an ultrasonic probe as an ultrasonic transmitter-receiver, for example. As illustrated in FIG. 2, the ultrasonic probe 2 includes an ultrasonic transmitting and receiving element 5 having a transducer (piezoelectric body) 3 for ultrasonic flaw detection and electrodes 4 provided on an upper and a lower surface of the transducer 3. The ultrasonic transmitting and receiving element 5 is disposed on a wave receiving plate 6 and is housed in a case 7 in this state. The electrodes 4 of the ultrasonic transmitting and receiving element 5 are electrically connected to a connector 8 provided at the case 7. Constituent materials, structures, and so on of the transducer 3, the ultrasonic transmitting and receiving element 5, the wave receiving plate 6, and so on can be those used in a known ultrasonic probe and are not particularly limited. When the sonic probe 2 is the sonic receiver such as the AE sensor, the same constitution as that of the ultrasonic probe is employed except that a sonic receiving element having the transducer (piezoelectric body) 3 for receiving AE is used. In this case, the constituent materials, structures, and so on of the transducer 3 for receiving AE, the sonic receiving element, the wave receiving plate 6, and so on may be those of a known AE sensor.

When the ultrasonic probe is employed as the sonic probe 2, a voltage is applied from the electrodes 4 to the transducer 3, then ultrasonic waves are transmitted through the wave receiving plate 6, and reflected waves of the ultrasonic waves are received through the wave receiving plate 6. In the ultrasonic probe, a surface 6b of the wave receiving plate 6 on an opposite side of a surface 6a in contact with the ultrasonic transmitting and receiving element 5 is a transmitting surface and a receiving surface (transmitting and receiving surface) of the ultrasonic waves. When the AE sensor is employed as the sonic probe 2, the transducer 3 receives sound waves (elastic waves) generated by AE in the object to be inspected through the wave receiving plate 6. In the AE sensor, the surface 6b, which is on the opposite side of the surface 6a of the wave receiving plate 6 in contact with the sonic receiving element, is a receiving surface of the sound waves. In the sonic probe 2, the ultrasonic transmitting and receiving element or the sonic receiving element (hereinafter, referred to as a sonic element as a generic name) 5 is disposed on the wave receiving plate 6, and the surface 6b on the opposite side of the surface 6a, which is in contact with the sonic element 5, is the sonic function surface 2a constituting at least one of the transmitting surface and the receiving surface of the sound waves (functioning as at least one of the transmitting surface and the receiving surface).

A contact member 9 functioning as a sonic propagation unit is provided on the sonic function surface 2a of the sonic probe 2. As enlargedly illustrated in FIG. 3, the contact member 9 includes a couplant 10 containing an elastomer and a sheet-shaped member 11 containing a polymer sheet. Here, a structure is illustrated where the sheet-shaped member 11 containing the polymer sheet is laminated to the couplant 10 containing the elastomer, but the sheet-shaped member 11 containing the polymer sheet is not limited thereto but may be any member having a sheet-shaped (sheet-like) shape. The sheet-shaped member 11 can be any sheet-shaped member containing a polymer and may be, for example, a polymer layer. In addition to being separated from the elastomer, a constituent material of the polymer sheet may be a polymer layer or the like formed by applying a surface treatment to the elastomer, for example, by a non-adhesive treatment (non-adhesive coating) by sliding coating or other treatments. The polymer layer formed by the non-adhesive treatment has a thickness of 30 μm or more, for example. The sheet-shaped member 11 may be formed and constituted in any way.

Figure 3:
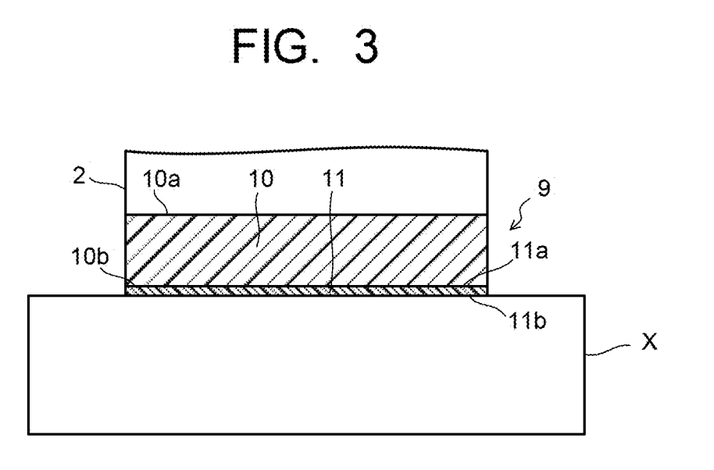
FIG. 3 is a cross-sectional diagram enlargedly illustrating a first example of a combination of the sonic probe and a contact member in the sonic inspection device illustrated in FIG. 1.

The couplant 10 has a first surface 10a in contact with the sonic function surface 2a of the sonic probe 2 directly or while interposing an intermediate member and a second surface 10b on an opposite side of the first surface 10a. The first surface 10a of the couplant 10 may have adhered to the sonic function surface 2a of the sonic probe 2 directly or while interposing the intermediate member with a not-illustrated adhesive. Examples of the intermediate member include a shoe made of a polymeric material, a joining layer, and the like. The sheet-shaped member 11 has a third surface 11a laminated with the couplant 10 to be in contact with the second surface 10b and a fourth surface 11b on an opposite side of the third surface 11a. The third surface 11a of the sheet-shaped member 11 may have adhered to the second surface 10b of the couplant 10 with a not-illustrated adhesive. The fourth surface 11b of the sheet-shaped member 11 constitutes a contact surface with an object X to be inspected (object to be handled).

Figure 4:
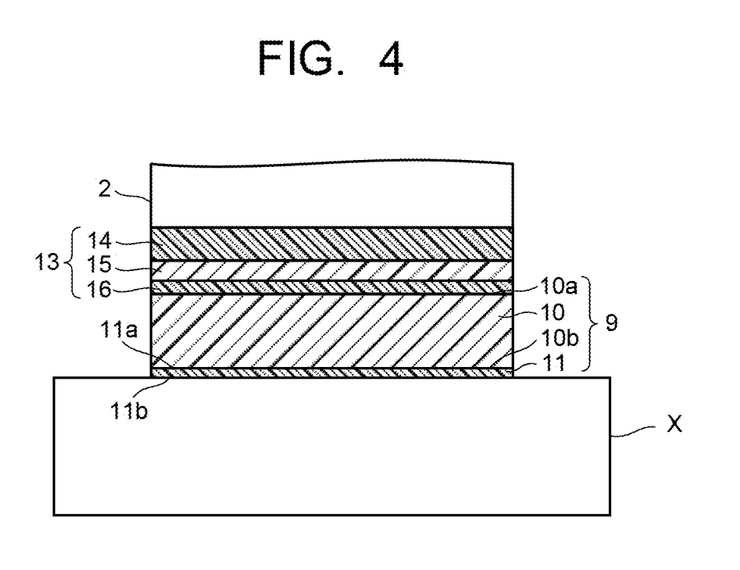
FIG. 4 is a cross-sectional diagram enlargedly illustrating a second example of the combination of the sonic probe and the contact member in the sonic inspection device illustrated in FIG. 1.

The sonic probe 2 and the contact member 9 may be joined by a joining layer 13 disposed between the sonic function surface 2a and the first surface 10a, for example, as illustrated in FIG. 4. The joining layer 13 has a constitution where, for example, a first adhesive layer 14 with reversibility, a polymer layer 15, and a second adhesive layer 16 are disposed in this order. Each of these layers 14, 15, and 16 will be described in detail later, arid by using the first adhesive layer with reversibility (reversible adhesive layer) 14, it is possible to easily attach and detach the contact member 9 to and from the sonic probe 2. For example, the object X to be inspected is not limited to a bulk solid, but may also be an aggregate of powders or a pressed powder. In such an inspection, the powder as the object X to be inspected adheres to the contact member 9, and it may be necessary to replace the contact member 9. By easily attaching and detaching the contact member 9 to and from the sonic probe 2, it is possible to increase the inspection efficiency of the object X to be inspected, such as the aggregate of powders.

The sonic inspection device 1 is disposed such that the fourth surface 11b of the sheet-shaped member 11 is in contact with the object X to be inspected. The sonic inspection device 1 has a load applying jig 12 provided on the sonic probe 2. in the sonic inspection device 1, a load is first applied to the sonic probe 2 through the load applying jig 12 and the load is further applied to the contact member 9 through the sonic probe 2. As will be described later, the couplant 10 is brought into contact with the object X to be inspected while interposing the sheet-shaped member 11 by the load applied to the contact member 9. This enables efficient propagation of sound waves between the couplant 10 and the object X to be inspected through the sheet-shaped member 11.

In addition, the sheet-shaped member 11 containing an ultra-thin, non-adhesive polymer sheet provided as a dry couplant on the surface 10b of the couplant 10, allows the sonic inspection device 1 to move on the object X to be inspected in a sliding state as described below, without removing the load by the load applying jig 12. This allows the sonic inspection device 1 to be easily moved to a next position of the object X to be inspected without removing the load by the load applying jig 12. The application of the load to the couplant 10 can be carried out by various mechanisms that apply force to the couplant 10. For example, the load can be applied to the couplant 10 by a mechanism such as an electromotive actuator using a stepping motor or AC servomotor, or an actuator using hydraulic or pneumatic pressure. The actuator and so on and the load applying jig 12 constitute a loading mechanism.

When the load is applied to the contact member 9 by the load applying jig 12, the couplant 10 deforms to follow unevenness or the like of a surface of the object X to be inspected due to deforming properties of the couplant 10 containing at least the elastomer, that is, due to its ultra-low modulus of elasticity, large reversible deformation, viscoelasticity, and so on. The deformation of the couplant 10 caused by the applied load allows the couplant 10 to be in close contact with the object X to be inspected while interposing the sheet-shaped member 11. The adhesive elastomer is capable of well propagating sound waves such as ultrasonic waves similarly to a liquid couplant.

Therefore, by having the couplant 10 in close contact with the object X to be inspected while interposing the sheet-shaped member 11, sound waves can be propagated efficiently through the sheet-shaped member 11 between the couplant 10 and the object X to be inspected when the load is applied. The sheet-shaped member 11 containing the ultra-thin, non-adhesive polymer sheet inhibits an adhesive state with the object X to be inspected without impairing the propagation of ultrasonic waves or other sound waves, as described below. These make it possible to improve both accuracy of nondestructive inspection of the object X to be inspected by the sonic inspection device 1 and mobility of the sonic inspection device 1 on the object X to be inspected.

When frictional force of the elastomer is measured, friction is overwhelmingly large compared to that of other materials and in some cases, the friction exceeding 1 is observed. An origin of this large frictional force is due to the close adhesion of the elastomer to the object X to be inspected. This phenomenon is observed because a contact area becomes extremely large due to deformation. Even if an attempt is made to bring hard materials such as metals into contact with each other, only roughness being a very small part of their contact surfaces, concretely, only tips of minute projections come into contact. On the other hand, when the modulus of elasticity is low as in the elastomer, the adhesion force increases due to large deformation capacity even with the same load. Thus having a large practical (microscopical) contact area with the object X to be inspected while interposing the sheet-shaped member 11, the elastomer can transmit ultrasonic waves well. However, the elastomer that more easily transmits the ultrasonic waves has the larger frictional force and is more difficult to peel off. Therefore, in the contact member 9, the sheet-shaped member 11 is provided on the surface 10b of the couplant 10 as illustrated in FIG. 3 and FIG. 4, thereby facilitating the movement when the load is applied.

There are two types of elastomers used as the couplant 10: a thermosetting elastomer and a thermoplastic elastomer, and both can be used for the sonic inspection device 1 of the embodiment. The thermoplastic elastomer is a copolymer of two or more polymers with different temperature dependencies of the modulus of elasticity. The elastomer used for the sonic inspection device 1 of the embodiment has predetermined viscoelasticity and can closely follow a surface shape of an object, so the elastomer does not contaminate surroundings compared to other couplants such as water or oil. Since the elastomer is solid, it is easy to remove and can be reused. Young's modulus (elastic constant) of the elastomer is preferably 0.1 MPa or more and 10 MPa or less to eliminate an air layer intervening between the contact member 9 and the object X to be inspected by pressing the couplant 10 against the object X to be inspected.

When Young's modulus of the elastomer that constitutes the couplant 10 exceeds 10 MPa, followability to the surface of the object X to be inspected and ability to eliminate the air layer decrease. When Young's modulus of the elastomer is less than 0.1 MPa, the ability of the elastomer to maintain its shape or the like when the load is applied to the couplant 10 decreases. Yield stress, which is stress at which plasticity of a material starts, is desirably large, preferably 2 MPa or more, and further preferably 20 MPa or more. Tensile strength of the elastomer is also preferably large, and preferably 2 MPa or more. A thickness of the elastomer that constitutes the couplant 10 is preferably 10 mm or less. Although a suitable thickness varies depending on an acoustic impedance and Young's modulus of the elastomer that constitutes the couplant 10, propagation performance of ultrasonic waves, and the like can be improved when the thickness is approximately 0.5 mm or more and 2 mm or less.

Examples of the thermoplastic elastomer constituting the couplant 10 include a polystyrene-based thermoplastic elastomer (SSC, TPS), a polyolefin-based thermoplastic elastomer (TPO), a vinyl chloride-based thermoplastic elastomer (TPVC), a polyurethane-based thermoplastic elastomer (TPU), a polyester-based thermoplastic elastomer (TPEE, TPC), a polyamide-based thermoplastic elastomer, and the like. Examples of the thermosetting elastomer include styrene-butadiene rubber (SBR), isoprene rubber (IR), butadiene rubber (BR), chloroprene rubber (CR), and acrylonitrile-butadiene rubber (NSR) which are classified as diene-based rubber, and butyl rubber such as isobutylene-isoprene rubber (IIR), ethylene-propylene rubber (EPM), ethylene-propylene-diene rubber (EPDM), urethane rubber (U), silicone rubber, and fluorine rubber (FKM) which are classified as non-diene-based rubber. Examples of other rubber materials include chlorosulfonated polyethylene (CSM), chlorinated polyethylene (CM), acrylic rubber (ACM), polysulfide rubber (T), epichlorohydrin rubber (CO, ECO), and the like. Since these materials have different properties such as heat resistance, abrasion resistance, oil resistance, and chemical resistance, it is preferable to select an appropriate material as required for each inspection object. Depending on the use, a mixture of a plurality of elastomers may be used. An additive having a size not preventing the transmission of sound waves, that is, having a diameter of approximately 200 μm or less may be mixed therein.

The elastomer constituting the couplant 10 more preferably includes at least one selected from the group consisting of polyester-based thermoplastic elastomer, styrene-butadiene rubber, isoprene rubber, butadiene rubber, chloroprene rubber, acrylonitrile-butadiene rubber, isobutylene-isoprene rubber, ethylene-propylene nibber, ethylene-propylene-diene rubber, silicone rubber, fluorine rubber, chlorosulfonated polyethylene, acrylic rubber, and epichlorohydrin rubber, which have excellent heat resistance.

As a material constituting the sheet-shaped member 11, a material larger in Young's modulus than the elastomer constituting the couplant 10 is used, and for example, the sheet-shaped members made of polyester, polyolefins such as polyethylene and polypropylene, fluorocarbon resins such as polytetrafluoroethylene, polychlorotrifluoroethylene, polyvinylidene fluoride, polyvinyl fluoride, polyphenylene sulfide, polyvinylidene chloride, and the like are used. By disposing such a non-adhesive polymer sheet as the sheet-shaped member 11 on the surface of the couplant 10, it is possible to move the sonic inspection device 1 on the object X to be inspected in the sliding state without removing the load on the couplant 10. The non-adhesiveness described here means that when a medium is in contact with an inspection object, it can be easily peeled off from the inspection object when the medium is moved perpendicular to the inspection object. Young's modulus of the polymer is more preferably 100 MPa or more to enhance the sliding ability. Young's modulus of the polymer sheet is preferably 2000 MPa or less to improve the followability to the surface irregularities or the like of the object X to be inspected.

Figure 5:
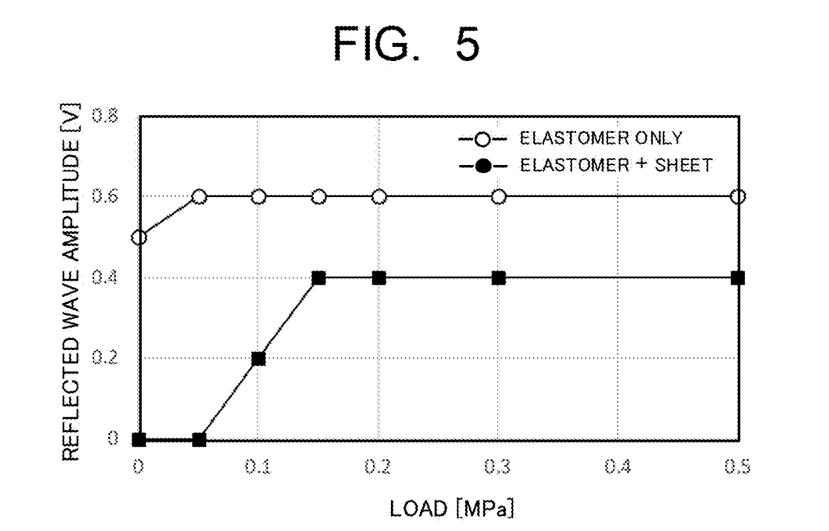
FIG. 5 is a diagram illustrating measured results of reflected wave amplitude by the contact member of the sonic inspection device of the embodiment.

FIG. 5 illustrates measured results of reflected wave amplitude when ultrasonic waves are irradiated from the sonic probe 2 to the object X to be inspected in the cases when the couplant 10 containing the elastomer and the sheet-shaped member 11 containing the polymer sheet are provided on the sonic function surface 2a of the sonic probe 2 and when only the couplant 10 containing the elastomer is provided on the sonic function surface 2a of the sonic probe 2. The elastomer member and polymer sheet used here will be described in detail in Example 1 below. As illustrated in FIG. 5, the use of the laminated elastomer and polymer sheet results in a slight decrease in the reflected wave amplitude compared to the case of the elastomer only, but the reflected wave amplitude is practical for the sonic inspection device 1 when a certain amount of load is applied.

Figure 6:
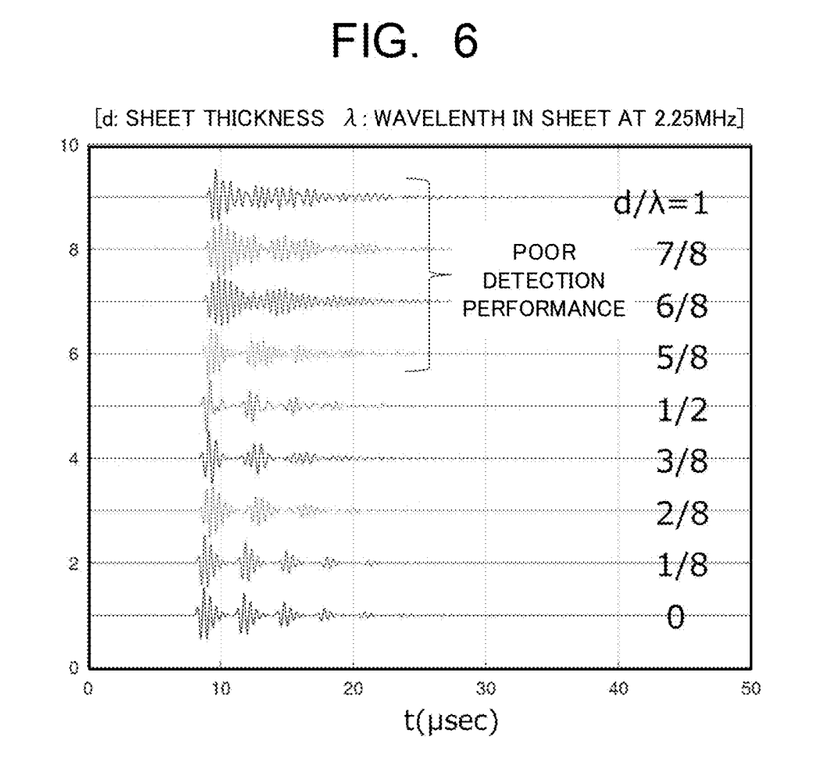
FIG. 6 is a diagram illustrating simulation results of a reflected signal by the contact member of the sonic inspection device of the embodiment.

The polymer sheet that constitutes the sheet-shaped member 11 preferably has a thickness of 1/250 or more and 1/2 or less of a wavelength λ of sound waves propagating through the sheet. By using the polymer sheet with such a thickness, ultrasonic waves or the like can be propagated well between the sonic probe 2 and the object X to be inspected through the contact member 9 having the couplant 10 and the sheet-shaped member 11. FIG. 6 illustrates simulation results of a reflected signal when a ratio of a thickness d of the polymer sheet to the wavelength λ in the polymer sheet (d/λ) at 2.25 MHz is varied from 0 to 1 by 1/8. As illustrated in FIG. 6, detection performance by ultrasonic waves or the like can be improved by setting the polymer sheet to have the thickness d that satisfies the d/λ ratio of 1/2 or less.

A sonic speed in the polymer sheet is generally around 1800 m/s to 2500 m/s, although there are differences depending on the constituent materials of the polymer sheet. In the nondestructive inspection, sound waves with a frequency of 1 MHz or more are mainly used. When the frequency is 1 MHz, 10 μm is approximately 1/250 of the wavelength because the wavelength λ in the polymer sheet is 2.5 mm when the sonic speed is 2500 m/s. In practical use, when the thickness of the polymer sheet is less than 10 μm, the polymer sheet may be easily damaged by minute irregularities of the object X to be inspected depending on a surface condition of the object X to be inspected. A concrete thickness of the polymer sheet is preferably 10 μm or more and 1 mm or less. Furthermore, by using the polymer sheet with such a thickness, the sonic inspection device 1 can be moved on the object X to be inspected in the sliding state while following the surface irregularities or the like of the object X to be inspected without removing the load on the couplant 10 at the inspection time.

As described above, in the sonic inspection device 1 of the embodiment, the couplant 10 containing the elastomer and the sheet-shaped member 11 containing the polymer sheet are provided on the sonic function surface 2a of the sonic probe 2 as the contact member 9. In the contact member 9, the couplant 10 containing the elastomer becomes in close contact with the object X to be inspected when the load is applied, so that sound waves such as ultrasonic waves can be propagated well between the sonic probe 2 and the object X to be inspected. Therefore, the accuracy of the nondestructive inspection by the sonic inspection device 1 can be improved. Furthermore, the polymer sheet provided as the sheet-shaped member 11 on the surface of the couplant 10 does not impair the propagation of ultrasonic waves or the like and thus does not impair the accuracy of the nondestructive inspection. In addition, the sonic inspection device 1 can be moved on the object X to be inspected in the sliding state without removing the load on the couplant 10 by using the polymer sheet as a dry couplant to the object X to be inspected. This reduces the time and man-hours required to remove the load when moving the sonic inspection device 1. Therefore, it is possible to improve the efficiency of the inspection process using the sonic inspection device 1.

In the joining layer illustrated in FIG. 4, the first adhesive layer with reversibility (reversible adhesive layer) 14 contains, for example, any one of a thermosensitive adhesive, a photo-irradiation curing agent, a heat foaming agent, a thermal expansion agent, and a photo structure change agent, which causes changes in adhesive strength due to stimulus and environmental changes. By providing the reversible adhesive layer 14, the contact member 9 can be quickly removed from the sonic probe 2 by using photo-irradiation, temperature change, and the like when desired. The polymer layer 15 and the second adhesive layer 16 are provided between the reversible adhesive layer 14 and the couplant 10, which may be necessary when integrating both of them, and are provided as necessary.

The reversible adhesive layer 14 preferably has a thickness of, for example, 10 μm or more and 100 μm or less. An example of the reversible adhesive layer includes a thermosensitive adhesive layer whose adhesiveness decreases at low temperatures. The thermosensitive adhesive layer contains a side-chain crystalline polymer as a main component, and when cooled to less than a melting point of the side-chain crystalline polymer, the adhesive strength decreases due to crystallization of the side-chain crystalline polymer. As the side-chain crystalline polymer, for example, various methacrylic resins with side-chain crystallinity are used.

Another example of the reversible adhesive layer 14 includes a thermosensitive adhesive layer whose adhesiveness decreases at high temperatures. The thermosensitive adhesive layer is known to contain the side-chain crystalline polymer and a foaming agent. The thermosensitive adhesive layer contains the side-chain crystalline polymer as a main component and the foaming agent at a ratio of 1 to 60 parts by weight to 100 parts by weight of the side-chain crystalline polymer. When the thermosensitive adhesive layer is heated to a foaming temperature or more of the foaming agent, the side-chain crystalline polymer becomes fluid, cohesive force of the adhesive layer decreases, and the foaming agent foams and expands, thereby enabling the contact member 9 to be easily removed from the sonic probe 2.

An example of the side-chain crystalline polymer includes methacrylate-based resin. Chemical and physical foaming agents can be used as the foaming agent. Examples of the chemical foaming agent include pyrolytic and reactive organic foaming agents, as well as inorganic foaming agents. The pyrolytic organic foaming agents include, for example, various azo compounds, nitroso compounds, hydrazine derivatives, and the like. The reactive organic foaming agent includes, for example, an isocyanate compound, and the like. The pyrolytic inorganic foaming agents include, for example, bicarbonates, carbonates, and the like. As other foaming agents, commercially available microencapsulated thermally expandable fine particles can be used. An average particle diameter of the foaming agent is preferably 5 to 50 µm.

A still another example of the reversible adhesive layer 14 includes a photo-curing peeling layer. The photo-curing peeling layer contains, for example, 100 parts by weight of the methacrylic polymer, which is a side-chain crystalline block copolymer, and 0.1 to 2 parts by weight of a photopolymerization initiator. Furthermore, one type of photopolymerization initiator may be used alone, or two or more types of photopolymerization initiators may be used together.

The polymer layer 15 is preferably in a film form. The term "film form" is not limited to film alone, but includes films, sheets, and the like as long as the effects of the embodiments are not impaired. Constituent materials of the polymer layer 15 include, for example, polyethylene, polyethylene terephthalate, polypropylene, polyester, polyamide, polyimide, polycarbonate, ethylene vinyl acetate copolymer, ethylene ethyl acrylate copolymer, ethylene-polypropylene copolymer, polyvinyl chloride, and other synthetic resins. The polymer layer 15 may be either a single layer body or a multi-layered body, and its thickness is preferably 5 to 250 µm. The polymer layer 15 may be subjected to surface treatment such as corona discharge treatment, plasma treatment, blasting treatment, chemical etching treatment, primer treatment, for example, to improve adhesion with the second adhesive layer 16.

The second adhesive layer 16 is provided to make the polymer layer 15 adhere to the couplant 10, which contains the elastomer. For example, a rubber-based solvent adhesive can be used as the second adhesive layer 16. An SBS (styrene-butadiene-styrene) resin-based adhesive and a chloroprene rubber-based adhesive can be used for the rubber-based solvent adhesive. At the time of adhesion, surface treatment such as corona discharge treatment, plasma treatment, blasting treatment, chemical etching treatment, primer treatment, for example, can be applied.

EXAMPLES

Examples and their evaluation results will be described below

Example 1, Comparative Example 1

First, an ultrasonic probe with a frequency of 2.25 MHz was prepared. A styrene-butadiene elastomer (containing process oil, hardness of JIS type E: 4, and a sonic speed under experimental conditions: 1350 m/s) was prepared as an elastomer member. A thickness of the elastomer member was 1 mm. A polyvinylidene chloride sheet (Young's modulus: 350 to 560 MPa, the sonic speed under experimental conditions: 1960 m/s) was prepared as a polymer sheet A. A thickness of the polymer sheet A was 10 µm, which corresponded to 1/100 of a wavelength in the sheet.

The polymer sheet A had adhered to the elastomer member with an ultra-thin SBS adhesive. A polymer layer (PET sheet) with a thickness of 20 µm had adhered to a surface on an opposite side of an adhesive surface of the polymer sheet A with the ultra-thin SBS adhesive. The PET sheet was laminated to the ultrasonic transmitting and receiving surface of the ultrasonic probe while interposing a reversible adhesive layer. In this way, the reversible adhesive layer, polymer layer, adhesive layer, elastomer member, and polymer sheet A were laminated to the ultrasonic probe in this order. The reversible adhesive layer used in this process was the thermosensitive adhesive layer whose adhesiveness decreases at high temperatures, and a layer with a thickness of 30 µm, where 100 parts by weight of the polymethacrylate-based resin and 10 parts by weight of microencapsulated thermally expandable fine particles (Expancel (registered trademark) manufactured by Japan Fillite Co., Ltd.) are mixed was used.

First, a shear tensile test was conducted to examine whether the probe could be moved while having only its own weight without a load further applied thereto. A load cell was connected to the ultrasonic probe and the resultant was placed on a stainless plate with a surface roughness Rz of 32 µm, the stainless plate was moved at a low speed, and a static friction coefficient was measured. As Comparative Example 1, the measurement was conducted only on the elastomer member to which the polymer sheet had not adhered. As a result, when the polymer sheet was not provided, the static friction coefficient was very high and it was difficult to move the ultrasonic probe. On the other hand, when the polymer sheet was provided, it was found out that the static friction coefficient was uniformly small and the ultrasonic probe could be moved.

Next, an ultrasonic flaw detection test was conducted. A carbon steel block with a length of 300 mm was prepared. The surface roughness Rz of a surface where ultrasonic waves were projected was set to 18 µm, and the surface roughness Rz of a surface where the ultrasonic waves bounced back was set to 1.6 µm. A load was applied to a 2.25 MHz vertical ultrasonic probe, which was pressed against the carbon steel block to conduct the flaw detection test. As Comparative Example 1, the flaw detection test was conducted on the ultrasonic probe with only the elastomer member installed. FIG. 5 illustrates an example of a relationship between the load and reflected wave amplitude. Under these experimental conditions, the reflected wave amplitude was obtained even with no load (0 MPa) in the case of the elastomer only, but when the polymer sheet A was present, the amplitude was approximately 1/10 of that of the signal of only the elastomer member by increasing the load to 0.015 MPa or more. This level of amplitude is sufficient for the flaw detection by adjusting a gain of a flaw detection test device.

Figure 7:
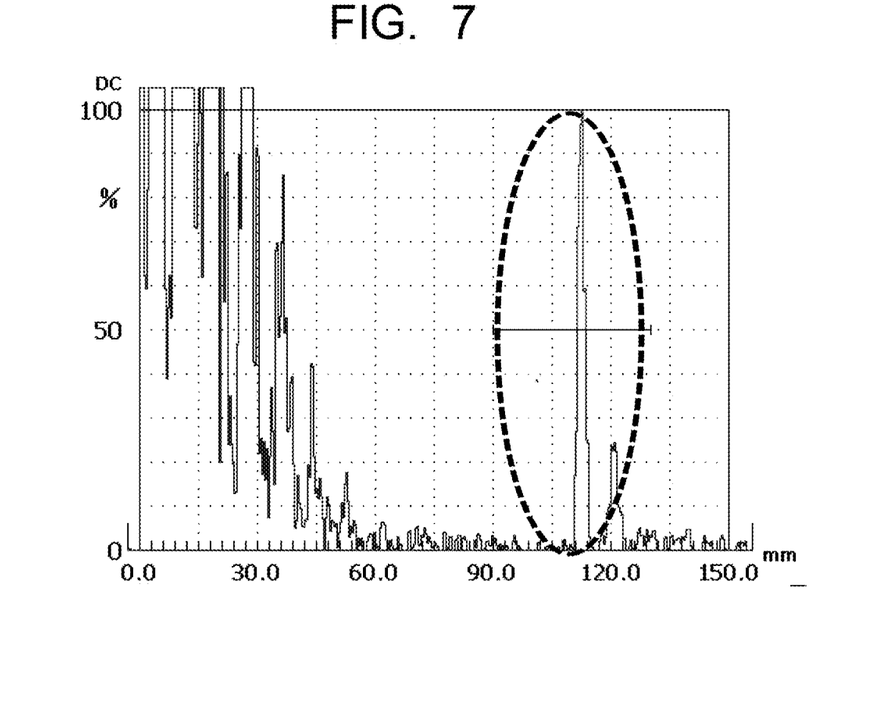
FIG. 7 is a diagram illustrating an example of a signal waveform obtained by a sonic inspection device in Example 1.

FIG. 7 illustrates a signal waveform obtained by the ultrasonic probe of Example 1. As illustrated in an area surrounded by a dotted ellipse in FIG. 7, the signal waveform was clearly obtained, indicating that performance of the ultrasonic probe was exhibited. Furthermore, when the probe was tried to be moved on the carbon steel block with the load applied by the actuator, it was confirmed that the probe could be easily moved while maintaining the amplitude. After the test, the contact member was heated with a dryer, and the contact member detached from the ultrasonic probe when the temperature reached 120° C. The contact member could be easily replaced.

Reference Example 1

A polyimide sheet (Young's modulus: 2100 MPa, the sonic speed under experimental conditions: 2450 m/s) was prepared as a polymer sheet B. A thickness of the polymer sheet B was 12.5 μm, which corresponded to $\frac{1}{100}$ of the wavelength in the sheet. The same ultrasonic probe and elastomer member as in Example 1 and the polymer sheet B were used, and the elastomer member and polymer sheet B were laminated to the ultrasonic probe in the same manner as in Example 1. The same shear tensile test as in Example 1 showed that the static friction coefficient was uniformly small even with the polymer sheet B and that the ultrasonic probe could be moved.

Figure 8:
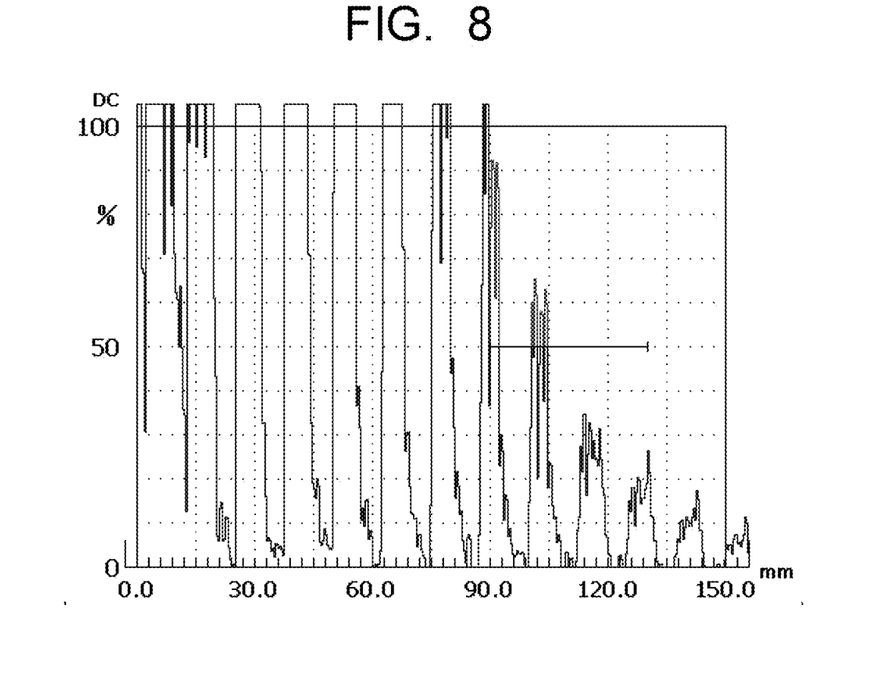
FIG. 8 is a diagram illustrating an example of a signal waveform obtained by a sonic inspection device in a reference example.

Next, the ultrasonic flaw detection test was conducted under the same conditions as in Example 1. FIG. 8 illustrates flaw detection results when the polymer sheet B was used. As illustrated in FIG. 7, a reflected wave signal was clearly observed with the polymer sheet A, whereas multiple reflections occurred between the elastomer member and polymer sheet B, and observation results were found to be insufficient with the polymer sheet B. This may be due to the fact that Young's modulus of the polymer sheet B was so large that it could not follow the unevenness of the surface roughness of the carbon steel block and an air layer was created therebetween. Therefore, Young's modulus of the polymer sheet is preferably 2000 MPa or less.

Constituent materials of the polymer sheet can be materials formed by applying surface treatment to the elastomer, for example, by a non-adhesive treatment by sliding coating (non-adhesive treatment requires a thickness of 30 μm or more, for example) or other treatments in addition to the material separated from the elastomer, and the same effect can be obtained. The polymer sheet may be formed and constituted in any way. Further, an adhesive layer may be present between the ultrasonic probe and the elastomer member, and between the elastomer member and the polymer sheet.

Comparative Example 2

The ultrasonic flaw detection test was conducted under the same conditions as in Example 1 with a constitution where only the polymer sheet A was disposed on the same ultrasonic probe as in Example 1. A load of up to 0.5 MPa was applied, but no flaw detection signal was obtained at all.

While certain embodiments of the present invention have been described, these embodiments have been presented by way of example only, and are not intended to limit the scope of the inventions. The novel embodiments described herein may be embodied in a variety of other forms, furthermore, various omissions, substitutions, changes, and so on may be made therein without departing from the spirit of the inventions. The accompanying claims and their equivalents are intended to cover such forms or modifications as would fall within the scope and spirit of the inventions.

What is claimed is:

1. A sonic inspection device comprising:
a sonic probe including a transducer configured to perform at least one of transmitting a sound wave or receiving a sound wave, and that has a sonic function surface constituting at least one of a transmitting surface of the sound wave or a receiving surface of the sound wave;
a contact member including a couplant and a sheet-shaped member, the couplant having a first surface, which is in contact with the sonic function surface of the sonic probe directly, and a second surface on an opposite side of the first surface, and containing an elastomer, and the sheet-shaped member laminated with the couplant to be in contact with the second surface and containing a polymer; and
a loading mechanism configured to apply a load to the contact member wherein
the contact member is disposed such that the polymer not having adhesiveness to an object to be inspected in the sheet-shaped member comes into contact with the object,
the polymer includes at least one selected from the group consisting of polyester, polytetrafluoroethylene, polychlorotrifluoroethylene, polyvinylidene fluoride, polyvinyl fluoride, polyphenylene sulfide, and polyvinylidene chloride,
the sheet-shaped member has a thickness of $\frac{1}{250}$ or more and $\frac{1}{8}$ or less of a wavelength λ of the sound wave propagating in the polymer, and
the elastomer contained in the couplant has a Young's modulus of 2 MPa or more and 10 MPa or less, and the polymer contained in the sheet-shaped member has Young's modulus of 100 MPa or more and 2000 MPa or less.

2. The device according to claim 1, wherein
the sheet-shaped member includes a polymer sheet.

3. The device according to claim 1, wherein
the elastomer includes at least one selected from the group consisting of polyester-based thermoplastic elastomer, styrene-butadiene rubber, isoprene rubber, butadiene rubber, chloroprene rubber, acrylonitrile-butadiene rubber, isobutylene-isoprene rubber, ethylene-propylene rubber, ethylene-propylene-diene rubber, silicone rubber, fluorine rubber, chlorosulfonated polyethylene, acrylic rubber, and epichlorohydrin rubber.

4. The device according to claim 1, wherein
the sonic probe is an ultrasonic transducer.

5. A sonic inspection method comprising:
disposing a sonic probe including a transducer configured to perform at least one of transmitting a sound wave or receiving a sound wave, and that has a sonic function surface constituting at least one of a transmitting surface of the sound wave or a receiving surface of the sound wave, on an object to be inspected while interposing a contact member including a couplant and a sheet-shaped member, the couplant being in contact with the sonic function surface of the sonic probe directly and containing an elastomer and the sheet-shaped member laminated with the couplant and containing a polymer, such that the polymer not having adhesiveness to the object in the sheet-shaped member comes into contact with the object;
applying a load to the contact member and pressing the couplant to bring into contact with the object through the sheet-shaped member;
conducting a nondestructive inspection of the object with the sonic probe using sound wave while pressing the contact member against the object, and
moving the sonic probe on the object while keeping the sheet-shaped member in contact with the object with the load applied to the contact member, wherein the polymer includes at least one selected from the group consisting of polyester, polytetrafluoroethylene, polychlorotrifluoroethylene, polyvinylidene fluoride, polyvinyl fluoride, polyphenylene sulfide, and polyvinylidene chloride, the sheet-shaped member has a thickness of 1/250 or more and 1/8 or less of a wavelength λ of the sound wave propagating in the polymer, and the elastomer contained in the couplant has a Young's modulus of 2 MPa or more and 10 MPa or less, and the polymer contained in the sheet-shaped member has Young's modulus of 100 MPa or more and 2000 MPa or less.

6. The method according to claim 5, wherein the sheet-shaped member includes a polymer sheet.

7. The method according to claim 5, wherein the conducting the nondestructive inspection includes:
   transmitting ultrasonic wave used as the sound wave from the sonic probe to the object through the contact member, and
   receiving a reflected wave from the object by the sonic probe through the contact member.

8. A contact member which is used for a sonic probe of a sonic inspection device, comprising:
   a couplant containing an elastomer; and
   a sheet-shaped member provided to be laminated with the couplant and containing a polymer not having adhesiveness to an object to be inspected, wherein
   the polymer includes at least one selected from the group consisting of polyester, polytetrafluoroethylene, polychlorotrifluoroethylene, polyvinylidene fluoride, polyvinyl fluoride, polyphenylene sulfide, and polyvinylidene chloride,
   the sheet-shaped member has a thickness of 1/250 or more and 1/8 or less of a wavelength λ of a sound wave propagating in the polymer, and
   the elastomer contained in the couplant has a Young's modulus of 2 MPa or more and 10 MPa or less, and the polymer contained in the sheet-shaped member has a Young's modulus of 100 MPa or more and 2000 MPa or less.

9. The contact member according to claim 8, wherein the sheet-shaped member includes a polymer sheet.

10. The contact member according to claim 8, wherein the elastomer includes at least one selected from the group consisting of polyester-based thermoplastic elastomer, styrene-butadiene rubber, isoprene rubber, butadiene rubber, chloroprene rubber, acrylonitrile-butadiene rubber, isobutylene-isoprene rubber, ethylene-propylene rubber, ethylene-propylene-diene rubber, silicone rubber, fluorine rubber, chlorosulfonated polyethylene, acrylic rubber, and epichlorohydrin rubber.

11. A sonic inspection device comprising: a sonic probe including a transducer configured to perform at least one of transmitting a sound wave or receiving a sound wave, and that has a sonic function surface constituting at least one of a transmitting surface of the sound wave or a receiving surface of the sound wave; a contact member including a couplant and a sheet-shaped member, the couplant having a first surface, which is in contact with the sonic function surface of the sonic probe while interposing an intermediate member, and a second surface on an opposite side of the first surface, and containing an elastomer, and the sheet-shaped member laminated with the couplant to be in contact with the second surface and containing a polymer; and a loading mechanism configured to apply a load to the contact member, wherein the contact member is disposed such that the polymer no having adhesiveness to an object to be inspected in the sheet-shaped member comes into contact with the object, the polymer includes at least one selected from the group consisting of polyester, polytetrafluoroethylene, polychlorotrifluoroethylene, polyvinylidene fluoride, polyvinyl fluoride, polyphenylene sulfide, and polyvinylidene chloride, and the intermediate member includes a joining layer including a first adhesive layer with reversibility; wherein the sheet-shaped member has a thickness of 1/250 or more and 1/8 or less of a wavelength λ of sound wave propagating in the polymer, the elastomer contained in the couplant has a Young's modulus of 2 MPa or more and 10 MPa or less, and the polymer contained in the sheet-shaped member has Young's modulus of 100 MPa or more and 2000 MPa or less.

12. The device according to claim 11, wherein the first adhesive layer contains any of a thermosensitive adhesive, a photo-irradiation curing agent, a heat foaming agent, a thermal expansion agent, and a photo structure change agent.

13. The device according to claim 11, wherein the joining layer further includes at least one selected from a polymer layer and a second adhesive layer.

* * * * *